(12) United States Patent
Abul-Khoudoud et al.

(10) Patent No.: US 8,568,763 B2
(45) Date of Patent: Oct. 29, 2013

(54) COMPOSITIONS AND COATINGS FOR DELIVERY OF THERAPEUTIC AGENTS

(75) Inventors: Omran R. Abul-Khoudoud, Ashland, KY (US); Catherine Cagiannos, Cincinnati, OH (US); Waldemar G. DeRijk, Bartlett, TN (US); Timothy C. Fabian, Memphis, TN (US); Lisa Kyle Jennings, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 13/484,086

(22) Filed: May 30, 2012

(65) Prior Publication Data
US 2012/0237585 A1 Sep. 20, 2012

Related U.S. Application Data

(63) Continuation of application No. 11/180,195, filed on Jul. 13, 2005, now Pat. No. 8,236,338.

(60) Provisional application No. 60/587,412, filed on Jul. 13, 2004.

(51) Int. Cl.
*A61F 13/00* (2006.01)
*A61F 2/06* (2013.01)
*A61F 2/00* (2006.01)
*A61K 9/14* (2006.01)
*A61L 33/00* (2006.01)

(52) U.S. Cl.
USPC ........... 424/423; 424/422; 424/486; 524/548; 427/2.24; 427/2.25; 623/1.42

(58) Field of Classification Search
USPC ......... 424/422, 423, 486; 623/1.42; 427/2.24, 427/2.25
See application file for complete search history.

(56) References Cited

U.S. PATENT DOCUMENTS

| 4,459,252 A | 7/1984 | MacGregor |
| 4,713,244 A | 12/1987 | Bawa et al. |
| 4,777,199 A | 10/1988 | Ishii et al. |
| 4,959,417 A | 9/1990 | Miyazono et al. |
| 5,037,473 A | 8/1991 | Antonucci et al. |
| 5,348,998 A | 9/1994 | Ito et al. |
| 5,665,728 A | 9/1997 | Morris et al. |
| 5,683,249 A | 11/1997 | Ibsen et al. |
| 5,716,981 A | 2/1998 | Hunter et al. |

(Continued)

FOREIGN PATENT DOCUMENTS

| EP | 652017 B1 | 9/1999 |
| EP | 1140242 B1 | 10/2002 |

(Continued)

OTHER PUBLICATIONS

Office action dated Mar. 18, 2010 for U.S. Appl. No. 11/180,195.

(Continued)

*Primary Examiner* — Rachael E Bredefeld
(74) *Attorney, Agent, or Firm* — Wilson Sonsini Goodrich & Rosati

(57) ABSTRACT

Water-soluble polymeric adhesive compositions and their use as delivery vehicles for carrying therapeutic agents on implantable devices, such as vascular grafts, are disclosed. Use of drug-coated vascular grafts is demonstrated for delivery of the therapeutic agents in vivo, thereby inhibiting restenosis or neointimal hyperplasia of the vascular graft and inhibiting infection at the vascular graft site. Methods of forming the adhesive and making the coated vascular grafts are also disclosed.

11 Claims, 1 Drawing Sheet

A

B

(56) References Cited

U.S. PATENT DOCUMENTS

| | | | |
|---|---|---|---|
| 5,788,979 | A | 8/1998 | Alt et al. |
| 5,824,049 | A | 10/1998 | Ragheb et al. |
| 5,843,348 | A | 12/1998 | Giordano |
| 5,876,743 | A | 3/1999 | Ibsen et al. |
| 5,897,955 | A | 4/1999 | Drumheller et al. |
| 6,273,913 | B1 | 8/2001 | Wright et al. |
| 6,306,166 | B1 | 10/2001 | Barry et al. |
| 6,326,417 | B1 | 12/2001 | Jia |
| 6,335,029 | B1 | 1/2002 | Kamath et al. |
| 6,544,544 | B2 | 4/2003 | Hunter et al. |
| 6,641,611 | B2 | 11/2003 | Jayaraman |
| 6,709,455 | B1 | 3/2004 | Chouinard |
| 6,726,923 | B2 | 4/2004 | Iyer et al. |
| 6,733,768 | B2 | 5/2004 | Hossainy et al. |
| 6,884,429 | B2 | 4/2005 | Koziak et al. |
| 6,890,546 | B2 | 5/2005 | Mollison et al. |
| 6,908,622 | B2 | 6/2005 | Barry et al. |
| 6,926,735 | B2 | 8/2005 | Henderson |
| 7,005,137 | B1 | 2/2006 | Hossainy et al. |
| 7,105,175 | B2 | 9/2006 | Schwarz |
| 7,176,261 | B2 | 2/2007 | Tijsma et al. |
| 7,223,286 | B2 | 5/2007 | Wright et al. |
| 7,247,313 | B2 | 7/2007 | Roorda et al. |
| 7,264,859 | B2 | 9/2007 | Rouns et al. |
| 7,297,159 | B2 | 11/2007 | Hossainy et al. |
| 7,300,662 | B2 | 11/2007 | Falotico et al. |
| 7,399,480 | B2 | 7/2008 | Mollison et al. |
| 7,442,721 | B2 | 10/2008 | Cheng et al. |
| 2003/0229392 | A1 | 12/2003 | Wong |
| 2003/0236342 | A1 | 12/2003 | Walz et al. |
| 2004/0039441 | A1 | 2/2004 | Rowland et al. |
| 2004/0148010 | A1 | 7/2004 | Rush |
| 2004/0193177 | A1 | 9/2004 | Houghton et al. |
| 2004/0197793 | A1 | 10/2004 | Hassibi et al. |
| 2004/0260318 | A1 | 12/2004 | Hunter et al. |
| 2005/0038455 | A1 | 2/2005 | Bates et al. |
| 2005/0058688 | A1 | 3/2005 | Boerger et al. |
| 2005/0177225 | A1 | 8/2005 | Hunter et al. |
| 2005/0220842 | A1 | 10/2005 | DeVitt et al. |
| 2005/0249776 | A1 | 11/2005 | Chen et al. |
| 2006/0039946 | A1 | 2/2006 | Heruth et al. |
| 2006/0052478 | A1 | 3/2006 | Madsen et al. |
| 2006/0134218 | A1 | 6/2006 | Abul-khoudoud et al. |
| 2006/0136051 | A1 | 6/2006 | Furst et al. |
| 2006/0182778 | A1 | 8/2006 | Balar et al. |
| 2006/0217797 | A1 | 9/2006 | Wong |
| 2006/0275338 | A1 | 12/2006 | Flugelman |
| 2007/0032864 | A1 | 2/2007 | Furst et al. |
| 2007/0134290 | A1 | 6/2007 | Rowland et al. |
| 2007/0244284 | A1 | 10/2007 | Cheng et al. |
| 2008/0008736 | A1 | 1/2008 | Glauser |
| 2008/0015322 | A1 | 1/2008 | Kindt-Larsen et al. |
| 2008/0132992 | A1 | 6/2008 | Bates et al. |
| 2008/0167711 | A1 | 7/2008 | Roorda |

FOREIGN PATENT DOCUMENTS

| | | |
|---|---|---|
| EP | 652017 B2 | 1/2004 |
| WO | WO 02/24247 A1 | 3/2002 |
| WO | WO 2004/014447 A1 | 2/2004 |
| WO | WO 2005/097227 A1 | 10/2005 |
| WO | WO 2005/097787 A2 | 10/2005 |
| WO | WO 2005/099787 A1 | 10/2005 |
| WO | WO 2005/097787 A3 | 1/2006 |
| WO | WO 2008/005439 A1 | 1/2008 |

OTHER PUBLICATIONS

Office action dated Mar. 19, 2009 for U.S. Appl. No. 11/180,195.
Office action dated Aug. 26, 2011 for U.S. Appl. No. 11/180,195.
Office action dated Sep. 16, 2008 for U.S. Appl. No. 11/180,195.
Office action dated Nov. 10, 2010 for U.S. Appl. No. 11/180,195.
Acetylsalicylic acid. Product identification and general description. http://chemicalland21.com/lifescience/phar/ACETYLSALICYLIC%20ACID.htm. Mar. 19, 2009.
Cagiannos et al. Rapamycin-coated expanded polytetrafluoroethylene bypass grafts exhibit decreased anastomotic neointimal hyperplasia in a porcine model. J of Vascular Surgery. Nov. 2005; 42(5):980-988.
Edwards et al. The effect of bacterial contamination on neointimal hyperplasia in vascular grafts. The American Surgeon. Dec. 2006; 72(12):1168-1175.
Fischer et al. Antibiotic Coated ePTFE Decreases Graft Colonization and Neointimal Hyperplasia. Journal of Surgical Research. 2009; 1-6.
Fischer, et al. Prosthetic vascular conduit in contaminated fields: a new technology to decrease ePTFE infections. Am Surg. Jun. 2008;74(6):524-8; discussion 528-9.
Holman, et al. Management of wound and left ventricular assist device pocket infection. Ann Thorac Surg. Sep. 1999;68(3):1080-2.
International search report dated Nov. 3, 2005 for PCT Application No. US2005/24670.
Lee et al. Coating with paclitaxel improves graft survival in a porcine model of haemodialysis graft stenosis. Nephrol Dial Transplant. 2007; 22:2800-2804.
Masaki, et al. Inhibition of neointimal hyperplasia in vascular grafts by sustained perivascular delivery of paclitaxel. Kidney Int. Nov. 2004;66(5):2061-2069.
Matl, et al. New anti-infective coatings of medical implants. Antimicrob Agents Chemother. Jun. 2008;52(6):1957-63.
Mohanty, et al. Use of antibiotic-loaded polymethyl methacrylate beads in the management of musculoskeletal sepsis—a retrospective study. J Orthop Surg (Hong Kong). Jun. 2003;11(1):73-9.
Murray, et al. Hierarchy of variables correlated to odontoblast-like cell numbers following pulp capping. J Dent. Sep.-Nov. 2002;30(7-8):297-304.

Figures 1A-D ns and Coatings for
Delivery of Therapeutic Agents

CROSS-REFERENCE

This application is a continuation application of U.S. application Ser. No. 11/180,195, filed on Jul. 13, 2005 now U.S. Pat. No. 8,236,338, which claims the benefit of priority of U.S. Provisional Application Ser. No. 60/587,412, filed Jul. 13, 2004, which are incorporated herein by reference in their entirety.

FIELD OF THE INVENTION

This invention relates to polymerizable compositions and their polymerization products, which may be used as drug delivery agents, particularly when used in combination with a vascular graft or other implantable device. Methods of making the coated vascular grafts and delivering therapeutic agents to a localized site in vivo are also disclosed.

BACKGROUND OF THE INVENTION

While autologous saphenous vein is the best conduit for peripheral arterial reconstruction, 30% of patients do not have this option due to prior vein harvest, trauma or phlebitis (Sayers et al., "Long-term Results of Femorotibial Bypass with Vein or Polytetrafluoroethylene," *Br. J. Surg.* 85:934-8 (1998)). Synthetic grafts made of expanded polytetrafluoroethylene (ePTFE) have been used as substitutes but have low patencies in vessels with diameters less than 6 mm because of early thrombosis or late graft failure from neointimal hyperplasia (Brewster et al., "Factors Affecting Patency of Femorotibial Bypass Grafts," *Surg. Gynecol. Obstet.* 157:437-42 (1983)). Infrapopliteal ePTFE grafts have primary patency rates at 4 years as low as 12% (Eagleton et al., "Femoral-Infrapopliteal Bypass With Prosthetic Grafts," *Surgery* 126: 759-65 (1999)).

Restenosis after percutaneous transluminal angioplasty (PTA) is a multifactorial response to local injury involving elastic recoil, negative arterial remodeling and neointimal formation. Stent technologies help to overcome elastic recoil and negative arterial remodeling associated with vessel injury, but there continues to be a 20-50% rate of restenosis because the continuing pressure exerted by stents against the vessel wall stimulates an increased arterial proliferative response (Beyar, "Novel Approaches to Reduce Restenosis," *Ann. NY Acad. Sci.* 1015:367-78 (2004)). One approach to combat neointimal hyperplasia utilizes elution of drugs with antiproliferative properties at the site of vessel injury. Coronary stents that elute rapamycin at the site of angioplasty have reduced neointimal hyperplasia as evidenced by decreased incidence of major adverse coronary events (MACE) and by reduction in binary restenosis, defined as a >50% diameter stenosis of the target lesion (Sousa et al., "Sustained Suppression of Neointimal Proliferation by Sirolimus-eluting Stents: One-year Angiographic and Intravascular Ultrasound Follow-up," *Circulation* 104:2007-11 (2001); Morice et al., "A Randomized Comparison of a Sirolimus-eluting Stent with a Standard Stent for Coronary Revascularization," *N Engl. J. Med.* 346:1773-80 (2002); Moses et al., "Sirolimus-eluting Stents Versus Standard Stents in Patients with Stenosis in a Native Coronary Artery," *N Engl. J. Med.* 349:1315-23 (2003); Holmes et al., "Analysis of 1-year Clinical Outcomes in the SIRIUS Trial: A Randomized Trial of a Sirolimus-Eluting Stent Versus a Standard Stent in Patients at High Risk for Coronary Restenosis," *Circulation* 109:634-40 (2004)). Stents have not performed as favorably in the infrainguinal circulation.

ePTFE is able to withstand the biomechanical forces that are exerted on it in the peripheral circulation without structural damage such as fractures that have been reported when stents are placed in the superficial femoral artery (Allie et al., "Nitinol Stent Fractures in the SFA," *Endovasc. Today* 3:22-34 (2004)). Non-textile ePTFE grafts are manufactured by an expansion process which transforms an initial full-density PTFE matrix into a structure composed of PTFE nodes interconnected by fine fibrils, which allow tissue ingrowth. The resulting expanded tube contains approximately 15% pure PTFE and 85% air by volume. The PTFE polymer is for the most part chemically inert; moreover, the grafts exhibit little tendency to dilate, have a strong electronegative luminal charge, and are hydrophobic until wetted by body fluids (Cannon, "The Expanded Reinforced Polytetrafluoroethylene Prosthetic Vascular Graft (ERPTFEVG)," In: *Vascular Grafting* (Wright et al., eds.), Boston, Bristol, London: John Wright—PSG Inc. (1983) at pp. 31-42). Coating ePTFE should not change the handling characteristics of the prosthetic because poor healing, inflammation and thrombosis may result.

Lacking from the prior art is an approach for coating ePTFE or other polymer grafts with a composition that will allow for delivery of one or more therapeutic agents to the graft site, which can thereby decrease neointimal hyperplasia by reducing tissue ingrowth and preserving anastomotic diameter.

The present invention is directed to achieving these objectives and overcoming the above-identified deficiencies in the art.

SUMMARY OF THE INVENTION

A first aspect of the present invention relates to a composition including: one or more volatile solvents, a first hydrophilic monomer component, and a second hydrophilic monomer component that is different from the first hydrophilic monomer component, wherein the first and second hydrophilic monomer components form a water-soluble polymerization product upon contact.

A second aspect of the present invention relates to a pharmaceutical formulation for providing extended release of a therapeutic agent. The pharmaceutical formulation includes a composition according to the first aspect of the invention, and a therapeutic agent.

A third aspect of the present invention relates to a water-soluble polymerization product of the pharmaceutical formulation according to the second aspect of the present invention.

A fourth aspect of the present invention relates to a delivery vehicle for providing the extended release of a therapeutic agent. The delivery device includes an implantable body having a surface, and a water-soluble polymerization product of the pharmaceutical formulation according the second aspect of the invention (i.e., the product according to the third aspect of the invention), where the water-soluble polymerization product is adhered to the surface of the implantable body.

According to a preferred embodiment, the implantable body is in the form of a vascular graft, such as an e-PTFE graft.

A fifth aspect of the present invention relates to a method of delivering a therapeutic agent to a surgical site in a patient. This method includes providing a delivery vehicle according to the fourth aspect of the invention and implanting the delivery vehicle at a surgical site within a patient, whereby upon implantation the water-soluble polymerization product dissolves to release the therapeutic agent. The delivery vehicles of the present invention are capable of afforded extended-release of the therapeutic agent over a period of time post-implantation.

According to a preferred embodiment, this method can be used to deliver a therapeutic agent to a vessel, i.e., where a preferred vascular graft has been implanted.

A sixth aspect of the present invention relates to a method of inhibiting restenosis or neointimal hyperplasia of a vascular graft. This method includes the step of performing the method according to the fifth aspect of the present invention, i.e., using a therapeutic agent that is able to inhibit restenosis or neointima formation at a vascular graft site. Upon release of the therapeutic agent, restenosis or neointima formation within the vascular graft is inhibited.

A seventh aspect of the present invention relates to a method of inhibiting infection at a vascular graft site. This method includes the step of performing the method according to the fifth aspect of the present invention, i.e., using a therapeutic agent that is able to inhibit infection. Upon release of the therapeutic agent, infection at the vascular graft is inhibited.

An eighth aspect of the present invention relates to a method of producing a drug delivery device of the present invention. This method includes the steps of providing an implantable body having a surface; and applying to the surface a pharmaceutical formulation according to the second aspect of the present invention, wherein the first and second hydrophilic monomer components polymerize to form a water-soluble polymerization product adhered to the surface.

A ninth aspect of the present invention relates to a system for preparing a water-soluble polymeric adhesive composition according to the first aspect of the present invention. The system includes: a first solution comprising one or more volatile solvents and a first hydrophilic monomer component dissolved in the one or more volatile solvents; and a second solution comprising one or more volatile solvents and a second hydrophilic monomer component that is different from the first hydrophilic monomer component and dissolved in the one or more volatile solvents, wherein either the first hydrophilic monomer component, the second hydrophilic monomer component, or both, are present in the first solution and second solutions, respectively, in amounts suitable to form a polymeric adhesive that is water-soluble.

The present invention relates to the use of adhesive formulations which have been modified to include a lower monomer content so as to form a polymerization product that is, surprisingly, water-soluble. The water-soluble polymerization product behaves as an adhesive for carrying therapeutic agents on an implantable device such as a vascular graft. The adhesive formulation can be applied to traditional ePTFE vascular grafts in manner that allows the adhesive to mechanically bind the ePTFE substrate, but without chemical interaction between the adhesive and the substrate. The adhesive formulation can be applied in a manner that does not alter the mechanical properties of the graft and will not interfere with the chemical activity of any therapeutic agent retained within the adhesive coating. The examples of the present invention demonstrate that rapamycin eluted from adhesive-coated ePTFE prosthetic grafts can decrease neointimal hyperplasia by reducing tissue ingrowth and preserving anastomotic diameter, and without increasing thrombosis or delaying healing. Rapamycin-eluting ePTFE grafts may allow use of prosthetic grafts in situations where autologous vein is unavailable and where neointimal hyperplasia is pronounced, such as in small diameter (<6 mm) vessels typical of infrapopliteal interventions.

BRIEF DESCRIPTION OF THE DRAWINGS

FIGS. 1A-D are scanning electron microscope images taken for the assessment of grafts.

DETAILED DESCRIPTION OF THE INVENTION

The present invention relates, in part, to water-soluble polymeric adhesives, including those containing therapeutic agents, compositions that can polymerize to form the water-soluble adhesives, and systems for preparing such compositions.

The water-soluble polymeric adhesive product of the present invention is the polymerization product of two or more component solutions, each containing a different hydrophilic monomer component dissolved in one or more volatile solvents. Upon combination of the two or more component solutions, the resulting product is rendered capable of polymerization for the various hydrophilic monomer components therein. It was found, quite surprisingly, that reducing the percentage of the monomer component in one or more of the component solutions allowed for the production of a water-soluble polymerization product. It is known, for example in the dental adhesive art, that commercially available solutions of the monomer components, when combined, are used to form permanent dental adhesives that are not water-soluble.

Thus, one aspect of the present invention relates to a system for preparing a water-soluble polymeric adhesive composition of the present invention. The system includes a first solution containing one or more volatile solvents and a first hydrophilic monomer component dissolved in the one or more volatile solvents, and a second solution containing one or more volatile solvents and a second hydrophilic monomer component that is different from the first hydrophilic monomer component and dissolved in the one or more volatile solvents. Either the first hydrophilic monomer component, the second hydrophilic monomer component, or both, are present in the first solution and second solutions, respectively, in amounts suitable to form a polymeric adhesive that is water-soluble. The system can further include additional components, as discussed below, for the formation of the polymerizable composition or the resulting polymerization product.

The polymerizable composition (i.e., prior to polymerization) is formed upon combining the first and second solutions, and includes one or more volatile solvents, the first hydrophilic monomer component, and the second hydrophilic monomer. Upon combining the first and second hydrophilic monomer components, they are capable of polymerization to form the water-soluble polymerization product.

The first and second hydrophilic monomer components can be any pair of monomers that are biocompatible. Preferred monomers include those traditionally used as dental adhesives, but where the concentration of one or both of the monomers in their respect solvent(s) is sufficiently low such that the resulting polymerization product, formed upon their combination, is rendered water-soluble. Without being bound by belief, it is expected that the use of reduced quantities of one or more hydrophilic monomers afforded a reduction in the final degree of polymerization, thereby reducing the average molecular weight of the final polymer and limiting the amount of cross-linking between the final polymer strands.

The first and second hydrophilic monomer components are preferably soluble in one or more of the following solvents: acetone, acetone and water, alcohols (preferably biocompatible alcohols such as ethanol), alcohol in water, and mixtures thereof (e.g., acetone and alcohol and water).

Preferred monomer components include hydrophilic methacrylates and dimethacrylates.

Exemplary hydrophilic methacrylate and dimethacrylate monomers that are soluble in acetone (or acetone in water) include, without limitation, N-tolylglycidal methacrylate (NTGMA), hydroxyethyl methacrylate (HEMA), bisphenyldimethacrylate (BPDM), triethyleneglycol dimethacrylate (TEGDMA), urethane dimethacrylate (UDMA), bisphenol-glycidyldimethacrylate (Bis-GMA), dipentaerythritol pentacrylate phosphate. The use of combinations of the methacrylates and dimethacrylates is also contemplated.

Exemplary hydrophilic methacrylate and dimethacrylate monomers that are soluble in alcohol (or alcohol in water) include, without limitation, BPDM, TEGDMA, UDMA, HEMA, copolymers of polycarboxylic acid (PCA), Bis-GMA, glycophosphoric acid dimethacrylate (GPDM), and 10-methacryloyloxymethacrylate (MDP). The use of combinations of the methacrylates and dimethacrylates is also contemplated.

By way of example only, the concentration of the first and second monomer components can individually vary between about 0.5 and about 20 percent by weight, more preferably between about 0.5 and about 18 percent, most preferably about 1 and about 16 percent. With respect to two preferred monomers, N-tolylglycidalmethacrylate can be present in an amount of about 3 weight percent or less, preferably about 0.5 to about 3 weight percent, and bisphenyldimethacrylate can be present in an amount of about 20 weight percent or less, preferably about 10 to about 20 weight percent. Water soluble polymerization products capable of extended delivery of therapeutic agents have been prepared in this manner.

In addition to the above components, the system and resulting composition can further include a suitable amount of a polymerization initiator. The initiator can be a photoinitiator or a chemical initiator. The polymerization initiator can either be introduced into one or both of the component solutions prior to their mixture, or introduced as a separate solution to the mixture of component solutions. The polymerization initiator is preferably present in an amount sufficient to reduce the time required to form the polymerization product (as compared to the rate of polymerization in the absence thereof). The amount of polymerization initiator will vary depending upon the type of initiator used, volatility of the one or more solvents used, and the conditions under which application of the composition to the implantable delivery device occurs (discussed below). That is, certain application procedures, such as spraying, will afford more rapid vaporization of the one or more volatile solvents. Persons of skill in the art will readily be able to identify optimal concentrations of the polymerization initiator depending upon these variables.

Suitable polymerization initiators are preferably soluble in the one or more volatile solvents. Exemplary polymerization initiators include, without limitation, camphorquinone, Duracure™ (available from Ciba Geigy) in conjunction with an aliphatic tertiary amine, a combination of benzoyl peroxide and a tertiary amine, and other proprietary photosensitizers. Where therapeutic agents are sensitive to light, i.e., the degrade under the dosage of light required to induce polymerization, photo initiators should not be used. Instead, chemical initiators or self-initiating monomers (such as BPDM) should be used.

The resulting water-soluble polymerization product (an adhesive) is intended to be used as a carrier or delivery vehicle for in vivo distribution of a therapeutic agent from an implantable delivery device. Thus, a further aspect of the present invention relates to a pharmaceutical formulation (i.e., the un-polymerized composition) as well as the adhesive product formed thereby, both of which contain one or more therapeutic agents.

With respect to the un-polymerized composition described above, the therapeutic agent is present in solution or suspension therein. The therapeutic agent is preferably though not necessarily dissolved in the one or more volatile solvents used to form the component solutions, i.e., prior to their mixing. Hence, the therapeutic agent should be at least partially soluble in the one or more volatile solvents described above.

Exemplary therapeutic agents include, without limitation, anti-inflammatory agents, antimicrobial agents, antibacterial agents, antifungal agents, anti-thrombogenic agents, anti-proliferative agents, and mixtures thereof.

Illustrative anti-inflammatory agents include classic non-steroidal anti-inflammatory drugs (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen, and mixtures thereof; COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof; the anti-inflammatory agent rapamycin; and mixtures thereof.

Antimicrotuble agents such as paclictaxel and docetaxel inhibit mitosis and, hence, cellular proliferation.

Antiproliferative agents such as cyclophosphamide, mithromycin, and actinomycin-D prevent proliferation of smooth muscle cells. Sirolimus, cyclosporine A, dexamethasone and methyl prednisolone are immunosuppressive agents that have been also shown to prevent or retard neointimal hyperplasia.

One preferred therapeutic agent for use with vascular grafts of the present invention is the anti-inflammatory/antibiotic agent rapamycin, which is partially soluble in acetone.

A further aspect of the present invention relates to a delivery vehicle for providing the extended release of a therapeutic agent. The delivery vehicle is an implantable body having a surface, and has adhered to its surface a water-soluble polymerization product of the pharmaceutical formulation of the present invention.

An exemplary delivery vehicle of the present invention is a vascular graft, although other implantable bodies can also be prepared in accordance with the present invention.

The preferred vascular grafts of the present invention can be formed of any suitable material, but preferably expanded polytetrafluoroethylene (ePTFE). Vascular grafts formed of ePTFE are substantially cylindrical in shape and porous. The grafts are characterized by a plurality of PTFE nodes and internodal fibrils. Together, the nodes and fibrils define the inner and outer surfaces of the graft, as well as a plurality of passages extending through the vascular graft. ePTFE grafts of the present invention can have the water-soluble polymerization product adhered to either the inner surface or the outer surface, or both. Preferably, the water-soluble polymerization product is applied to at least the inner surface of the ePTFE graft. The polymerization product is applied to the grafts in a manner that does not allow for clogging or covering of a substantial portion of the passages extending through the vascular graft. By substantial portion, it is intended that the coating on the vascular graft surface is not enough to interfere or disrupt the intended mechanical functioning of the graft.

The amount of therapeutic agent to be delivered by a particular delivery vehicle can vary from one therapeutic agent to another. Because delivery of the therapeutic agent is localized, the amount of the therapeutic agent loaded onto each delivery vehicle can be optimized based upon the solubility of the polymerization product, and the rate of therapeutic agent distribution into blood or tissue in which the delivery vehicle has been introduced. Measurements of these properties can be performed in accordance with the Examples infra. Thus, persons of skill in the art will be fully able to identify the amount of therapeutic agent to be loaded onto the delivery vehicle to achieve maximal efficacy using the lowest effective dosage.

The therapeutic agent is preferably present in an amount of between about 10 μg to about 1 g per implantable delivery device, more preferably about 100 μg to about 100 mg. The solubility of the therapeutic agent, however, is a limiting factor in the amount of therapeutic agent to be applied to the implantable device. That is, the solubility of the therapeutic agent in the one or more volatile solvents will dictate that amount of therapeutic agent that can practically be loaded into the water-soluble polymeric coating (adhesive) applied to the implantable device.

By way of example using the preferred vascular graft containing rapamycin, the rapamycin is preferably loaded onto the graft at an amount of between about 100 μg to about 100 mg per graft, more preferably about 500 μg to about 10 mg per graft, most preferably about 1000 μg (1 mg) per graft.

The pharmaceutical formulation can be applied, i.e., prior to substantial polymerization thereof, to the delivery vehicle using any appropriate procedure. Suitable application procedures include, without limitation, brushing, spraying, dipping, pouring, and combinations thereof. The application procedure can be performed as a single step or as multiple steps with intervening delays to allow partial or complete polymerization of the previously applied material. When multiple application steps are performed, multiple layers of the pharmaceutical formulation are applied to the delivery vehicle. When applied to vascular grafts, the layer(s) of the pharmaceutical formulation do not substantially obstruct the plurality of passages formed through the vascular graft.

Having prepared the implantable delivery device, the delivery device can be implanted into a surgical site in a patient for delivery of a therapeutic agent (embedded in the polymerization product applied thereto) as the water-soluble polymerization product dissolves. Upon dissolution of the water-soluble polymerization product, the therapeutic agent is administered to the patient.

With respect to the preferred delivery vehicles of the present invention, which is a vascular graft, they are intended to be surgically placed or installed with connections to one or more vessels of a patient. The vessel can be of any dimension for which vascular grafts are capable of being used. The vascular grafts of the present invention are particularly useful when employed on vessels of less than about six (6) mm in diameter. The vessel can be part of either the arterial or the venous system, preferably a vessel of the arterial system.

Depending upon the solubility of the pharmaceutical formulation, the therapeutic agent can be released over an extended period of time. The solubility of the pharmaceutical formulation can be controlled by the rate of application and the concentration of the polymerizing resins. With a low monomer concentration, the polymerization is initiated in the presence of an abundance of solvent and proceeds until all available carbon double bonds have been consumed while the solvent is still evaporating, leaving a porous polymer with little cross linked polymer strands and intertwined polymer strands. The final structure will have a large surface area which in turn makes it dissolve in blood and serum at an accelerated rate. When the polymerization time is exceeded by the evaporation time, the porous structure will form. The degree of porosity and the lack of intertwining and cross linking will determine the time for total dissolution. By varying the concentration of the resins, a time range of 2 days to six months was obtained in initial testing. By applying the adhesive in multiple thin layers, the adhesives could be applied with very low resin concentrations and still deliver sufficient bulk of material and therapeutic agent to have a therapeutic effect. In addition, the structure of multiple thin layers provides for a flexible layer, thereby greatly reducing the risk of cracking and flaking of the adhesive layer.

By controlling the release rate, the release of the therapeutic agent can be tailored to achieve the desired blood and/or tissue levels of the therapeutic agent for a desired period of time. For preferred delivery rates, the therapeutic agent is preferably released over a period of time that is two days or more, preferably from about 2 days to about 6 months, more preferably from about 2 to 3 days up to about 30 to 60 days.

As a consequence of administering therapeutic agents via a vascular graft of the present invention, the insertion of the vascular graft in a vascular site will allow for inhibition of restenosis or neointima formation within the vascular graft. By way of example, the administration of rapamycin or other anti-inflammatory agents (or combinations thereof) can inhibit restenosis and neointima formation.

As a consequence of administering therapeutic agents via a vascular graft of the present invention, the insertion of the vascular graft in a vascular site will allow for inhibition of infection of a vascular graft. By way of example, the administration of rapamycin or other antibiotic agents (or combinations thereof) can inhibit development of an infection at the vascular graft site.

EXAMPLES

The examples below are intended to exemplify the practice of the present invention but are by no means intended to limit the scope thereof.

Example 1

System of Component Solutions and Pharmaceutical Formulation Containing Rapamycin A two component system was prepared, which was then used to form a pharmaceutical formulation containing Rapamycin. The first solution (Component A) included NTGMA (1 wt %) in a volatile solvent containing 80% acetone, 14% ethanol, and 5% water. The second solution (Component B) included BPDM (16 wt %) and rapamycin (1 wt %) in a volatile solvent containing 70% acetone and 13% ethanol. For each of the component solutions, the hydrophilic monomer was dissolved in the one or more volatile solvents. For Component B, rapamycin was also dissolved in the acetone prior to forming the Component B solution.

Because BPDM auto-polymerizes, the use of or activation of a separate polymerization initiator was not necessary.

The use of hydrophilic monomer components is predicated on the active methacrylates found in dentin bonding agents. These acrylics were designed for bonding to the organic matrix in dentin and the inorganic phase in dental enamel. The modification of these adhesives to accommodate use with vascular grafts is believed to be novel and distinct application of these adhesives. Specifically, the adhesives of the present invention, unlike dentin bonding agents, are (far more) water soluble and, therefore, they dissolve in aqueous media to release the therapeutic agent.

Example 2

Coating ePTFE Graft With Polymeric Composition Containing Rapamycin

Upon combining Components A and B, the resulting polymerizable composition was applied to precut segments of 6 mm thin wall ePTFE grafts provided by Impra/Bard Peripheral Vascular (Tempe, Ariz.) for a distance of 1 cm at both ends on the luminal surface. The coating was applied by brushing to provide thin layers (5-10 microns thick) of the dilute monomers, with the solvent evaporating while polymerization of the monomers continued. Upon volatilizing the solvent, the drug was made available in microcrystalline form, mechanically locked in the polymer, and thus readily available when the polymer matrix was later dissolved. The repeated applications of dilute monomer solutions created a laminar structure with limited cross linking. Without being bound by belief, the inter-polymer spaces created by the molecular lamellae provided a means of swelling the polymer by aqueous attack and subsequent dissolution of the hydrophilic polymer. It is likewise believed that the mode of application achieved substantially uniform disbursement of the drug throughout the adhesive polymer.

Example 3

Examination of Coated ePTFE Grafts via Scanning Electron Microscopy

Figure 1A:
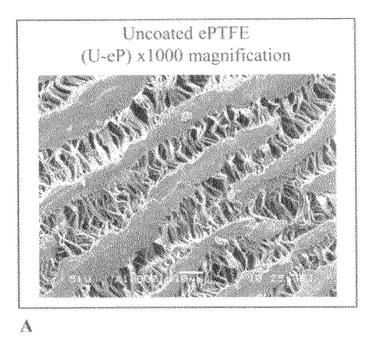
FIG. 1A illustrates an uncoated ePTFE graft (U-eP) at 1000×.
Figure 1B:
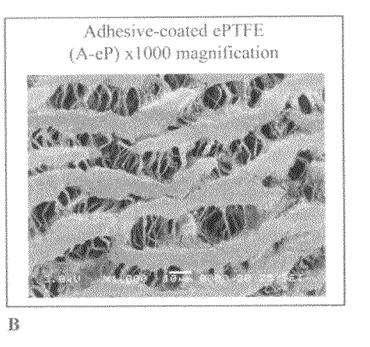
FIG. 1B illustrates an adhesive coated ePTFE graft (A-eP) at 1000×.
Figure 1C:
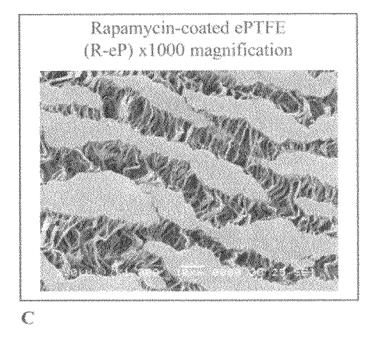
FIG. 1C illustrates a rapamycin-eluting, adhesive coated ePTFE graft (R-eP) at 1000×.
Figure 1D:
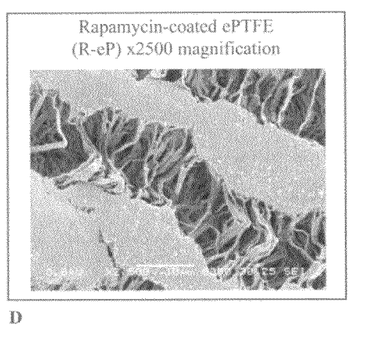
FIG. 1D illustrates a rapamycin-eluting, adhesive coated ePTFE (R-eP) at 2500×.

The ultrastructure of the ePTFE was assessed by scanning electron microscopy (SEM). Examining sections of coated grafts by SEM, the coating was found to be adherent to the nodal islands of the ePTFE and did not obliterate the internodal fibrils (FIG. 1). The SEM studies showed that rapamycin was encapsulated in the matrix of polymeric adhesives. Rapamycin appeared as speckling on nodal islands. The SEM studies did not show any other differences between rapamycin-coated grafts and those coated with adhesive alone. Handling characteristics of the graft material were maintained during suturing and implantation.

Example 4

Assessment of Rapamycin Elution from Coated ePTFE Grafts

The rapamycin was eluted over a 30 day period. The concentration of rapamycin was 250 g/cm$^2$ or 1 mg rapamycin per bypass graft.

Preimplantation and postexplantation grafts, blood and tissues were sent to the HPLC Drug Monitoring Laboratory at the University of Texas Medical School at Houston, (6431 Fannin, Suite 6.233, Houston Tex. 77030) for rapamycin level quantification. Analyses were performed using HPLC/UV assays developed by Dr Kimberly L. Napoli, the director of the laboratory (Napoli et al., "Distribution of Sirolimus in Rat Tissue," *Clin. Biochem.* 30:135-42 (1997), which is hereby incorporated by reference in its entirety). Whole blood was collected on the first three postoperative days and at euthanasia to quantitate systemic exposure to rapamycin. To confirm elution of rapamycin from the ePTFE and deposition of drug in the native arterial wall, explanted grafts and adjacent iliac artery were snap frozen in liquid nitrogen. The tissues were packaged on dry ice and sent for rapamycin quantification. The kinetics of elution were extrapolated by sacrificing nine animals (n=3 per time point) on postoperative day 7, 14 and 28. These animals were separate from the twenty-two animals used to evaluate for changes in neointimal hyperplasia.

Example 5

Implantation of Rapamycin-Eluting ePTFE Grafts

Grafts were sterilized with ethylene oxide prior to implantation. In preliminary experiments, rapamycin-eluting grafts were sent for drug quantification both pre and post ethylene oxide sterilization.

All animal care and procedures were performed in accordance with the guidelines of the University of Tennessee's Institutional Animal Care and Utilization Committee (IACUC). The animal procedures and care complied with the *Guideline for the Care and Use of Laboratory Animals* (National Institutes of Health Publ. No. 80-23 (1985). Twenty two mongrel pigs (Nichols hog farm, AK) were housed in the animal care facility of the Department of Comparative Medicine at the University of Tennessee. All animals were male and weighed from 17 to 27 kg. Food and water was provided ad libitum. Animals were fed 325 mg aspirin daily starting the day prior to surgery until euthanasia. Preoperatively animals were given 1 gram Cefazolin intravenously and Cephalexin 500 mg by mouth twice a day for the first five postoperative days. Aorto-iliac bypass grafts utilizing 6 mm thin wall ePTFE were performed under general anesthesia through a midline laparotomy. Anesthesia was induced with intramuscular telazol reconstituted with xylazine and was maintained with 1% isoflurane (Rhone-Poulenc, Bristol, England). Prior to arterial clamping, a bolus of heparin (110 units/kg) was administered intravenously after which supplemental heparin (55 units/kg) was given at 30 minute intervals until completion of surgery. The anastomoses were 12 mm in length and had an end to side configuration. The aortic anastomoses were performed with 6-0 polypropylene and the iliac anastomoses were performed with 7-0 polypropylene. The intervening native iliac artery was doubly ligated. The animals were divided into three groups: animals bypassed with uncoated ePTFE (U-eP: n=6); animals bypassed with adhesive coated ePTFE (A-eP: n=6); animals bypassed with rapamycin-eluting ePTFE (R-eP: n=10). All animals were euthanized on postoperative day 28.

At euthanasia, the bypass grafts and adjacent iliac and aortic segments were removed in continuity. The iliac artery was opened longitudinally along the vessel wall opposite the anastomosis, pinned to in vivo dimensions and placed in 10% formalin. Immediately after explantation, the length of the distal anastomosis was measured (heel to toe) and the percentage of maintained anastomotic length was calculated (explant anastomotic length/12). Two surgeons, not blinded to experimental groups, measured the explanted anastomotic length and averaged their values for each animal. Specimens were not perfusion fixed because samples were thin, usually 3-5 mm thick which allowed for rapid formalin fixation. All specimens were collected and processed in a similar fashion. Absolute measurements were not evaluated.

Variables examined relative proportions or ratios between groups. After a minimum of 24 hours of soaking in 10% formalin (Baxter Diagnostics, McGaw Park, Ill.), the iliac segments were cross sectioned at the heel and placed in cassettes. Paraffin processing was performed by pathology technicians from the Department of Pathology at the University of Tennessee Health Sciences Center. After paraffin embedding, two to three (five micrometers each) sections were stained with hematoxylin and eosin (H & E) or Masson's trichrome and used for orphometric analysis or pathologic grading.

Morphometric comparisons were made using Image J (1.30 version) software downloaded from the National Institute of Health's (NIH) website. Measurements were made from cross sections taken at the heel of the iliac anastomoses. Tissue blocks were generated from here because the hyperplastic response was most pronounced to the naked eye, and the sectioning resulted in a circular cross section of the ePTFE that allowed for consistency during pathologic grading and morphometric analysis. H & E or Masson's trichrome stained paraffin sections were mounted on slides and viewed with the 2× objective on a Zeiss microscope. Fields were photographed with a Camedia D-540 ZOOM digital camera (OLYMPUS). The digital images were analyzed with Image J (version 1.30) to determine differences in morphometric criteria of neointimal hyperplasia. The morphometry analysis was performed by a researcher blinded to experimental groups.

The percentage of cross sectional narrowing attributed to neointimal hyperplasia and the degree of neointimal thickness at the arterial—graft junction indexed to ePTFE graft thickness were compared between groups of animals. Percentage of cross sectional narrowing was calculated by dividing the neointimal area by the area bound by the inner table of the cross sectioned ePTFE. The neointimal area was calculated by subtracting the luminal area from the area bound by the inner table of the cross sectioned ePTFE (% cross sectional narrowing=internal ePTFE area—luminal area/internal ePTFE area). The intimal thickness index was calculated by dividing the thickness of neointima at the heel of the iliac anastomosis by the cross sectional thickness of the ePTFE graft. The measurement was performed where the internal elastic lamina of the native artery was disrupted by the polypropylene suture used to perform the anastomosis. Measurements for percentage of cross sectional narrowing and intimal thickness index were presented as mean values +/− standard errors of the mean (SE).

Semiquantitative histologic grading of H & E and Masson's trichrome sections was performed by a pathologist blinded to experimental groups (C. Handorf). Features examined included endothelialization, spindle cell ingrowth and neointimal formation. Grading was performed as follows: 0=none of the luminal circumference of the graft involved; 1=<25% of the luminal circumference of the graft involved; 2=25-75% of the luminal circumference of the graft involved; 3=>75% of the luminal circumference of the graft involved. Immunostains for β-actin and factor VIII-related antigen to identify SMCs and endothelial cells were not performed. The pathologist examined sections with the 40× power objective and identified endothelial cells based on surface location and flattened cellular morphology. Spindle cells were characterized with Masson's trichrome as elongated cells with purple cytoplasm that populated regions of extracellular matrix. Ingrowth of spindle cells was used to correlate with VSMC migration. Presence of spindle cells and extracellular matrix (ECM), which stains blue or pink with Masson's trichrome depending on collagen content, were used to designate areas of neointimal formation on the ePTFE inner surface.

Statistical analysis was performed using SAS 9.0 (SAS Institute Inc., Cary, N.C.) statistical software. First, preplanned contrasts in the context of one-way analysis of variance (ANOVA) (that are equivalent to 2-tailed t-tests with the square root of the mean square error used as the pooled standard deviation) were used to demonstrate that there was no statistical difference between the U-eP and the A-eP groups. Next, the data were combined into one control group (n=12). Finally, data from the R-eP group (n=10) were then compared with data from the combination of the U-eP and A-eP groups (n=12) (Table II), using two tailed unpaired t-tests with equal variances. Differences were considered significant at P<0.05. Variables are presented as means +/− standard errors of the mean (SE).

Reproducibility of measurements was assessed for percentage of cross sectional narrowing, ePTFE graft thickness, and ePTFE internal graft area. The pooled within animal standard deviation for percentage of cross sectional narrowing was 3.5%; the intraclass correlation coefficient was 0.84, indicating excellent reproducibility. For ePTFE graft thickness and area, the pooled within animal standard deviations were 0.08 mm and 1.40 mm$^2$ respectively. For ePTFE graft thickness the reproducibility was poor; however, the reproducibility of the ePTFE internal graft area was moderate, with an intraclass correlation coefficient of 0.71.

All animals survived to euthanasia with palpable pulses in the operated hindlimb and patent grafts. None of the animals developed wound or graft infections. Weight gain was similar. Aneurysmal degeneration was absent and all grafts were well incorporated. Animals bypassed with uncoated ePTFE grafts were compared to those bypassed with adhesive coated ePTFE to see if the vehicle for the rapamycin was responsible for any changes in the degree of neointimal hyperplasia. There were no differences in the length of the iliac anastomosis, the percentage of cross sectional narrowing or the intimal thickness index between the two groups at explantation (see Table I below). The coating appeared to be inert and was not associated with a propensity for inflammation or thrombosis. The data for the two groups were then combined to form one control group (U-eP and A-eP) for comparison to the animals bypassed with rapamycin-eluting ePTFE (R-eP).

TABLE I

Comparison of Gross Pathologic and Morphometric Parameters of Neointimal Hyperplasia Between Animals Treated with Uncoated (U-eP) and Adhesive Coated ePTFE (A-eP)

| POD 28 | U-eP (n = 6) | A-eP (n = 6) | P value |
|---|---|---|---|
| % Initial anastomotic length | 57.3 ± 3.2 | 63.8 ± 3.2 | 0.17 |
| % Cross sectional narrowing | 27.4 ± 4.0 | 29.7 ± 4.0 | 0.68 |
| Intimal thickness Index | 1.71 ± 0.20 | 1.79 ± 0.18 | 0.78 |

At euthanasia, animals treated with rapamycin-eluting ePTFE grafts had longer explanted iliac anastomoses (R-eP=10.3+/−0.26 mm vs U-eP & A-eP=7.3+/−0.15 mm; P<0.0001). In addition to having longer anastomoses (85.6% of initial anastomotic length maintained vs. 60.6%; P<0.0001), the R-eP animals and less cross sectional narrowing in the outflow graft (16.2% vs. 28.5%; P=0.0007) and decreased intimal thickness indexed to ePTFE (see Table II below).

TABLE II

Comparison of Gross Pathologic and Morphometric Parameters of Neointimal Hyperplasia Between Animals Treated with Uncoated (U-eP) and Adhesive Coated ePTFE (A-eP) and Rapamycin-eluting ePTFE (R-eP)

| POD 28 | U-eP & A-eP (n = 12) | R-eP (n = 10) | P value |
|---|---|---|---|
| % Initial anastomotic length | 60.6 ± 2.3 | 85.6 ± 2.5 | <0.0001 |
| % Cross sectional narrowing | 28.5 ± 2.7 | 16.2 ± 3.0 | 0.007 |
| Intimal thickness Index | 1.75 ± 0.13 | 1.22 ± 0.14 | 0.01 |

Complete endothelial coverage of ePTFE was noted in all groups. R-eP animals had less spindle cell ingrowth and neointimal formation. They received lower scores than U-eP and A-eP animals (see Table III below). Medial necrosis and aneurysmal degeneration were absent and there were no differences in cellular infiltration between the experimental groups.

TABLE III

Pathologic Grading of Anastomotic Cross Sections for Neointimal Hyperplasia

| R-eP vs. U-eP & A-eP | U-eP & A-eP (n = 12) | R-eP (n = 10) | P value |
|---|---|---|---|
| Neointimal formation | 2.5 ± 0.2 | 0.8 ± 0.2 | <0.0001 |
| Spindle cell ingrowth | 2.3 ± 0.3 | 0.8 ± 0.2 | 0.0007 |
| Endothelialization | 3.0 ± 0.0 | 3.0 ± 0.0 | 1 |

Preliminary experiments with waterbaths showed that the adhesive coating was subject to aqueous attack with dissolution over a 30 day period. SEM samples of explanted anastomoses showed coverage of the internal surface of the ePTFE with cells and biologic debris. The adhesive coating could not be visualized and comparisons of adhesive integrity and thickness between A-eP and R-eP samples could not be made. It is assumed that the neointima formed on ePTFE as dissolution of the adhesive polymeric matrix was occurring.

The ethylene oxide sterilization process did not cause loss of rapamycin prior to implantation. Similar drug levels were detected despite sterilization. Similarly, the rapamycin fraction was detected 18 minutes after instilling the sample onto the HPLC column irrespective of sterilization. Table IV (below) shows rapamycin levels obtained from grafts, explanted arteries and blood sampled at various time points. Preliminary HPLC experiments showed that the coating process resulted in loading of 1 mg of rapamycin per ePTFE graft prior to implantation. Results from 9 animals that were sacrificed temporally to help determine elution kinetics, showed that the majority of rapamycin eluted off grafts by one week. Levels decreased from 1000 μg preimplatation to 26.7 μg at one week post explantation. Drug (2.9 μg/gm) was detected in the adjacent arterial wall on postoperative day 7 and persisted until euthanasia. Despite being present in the arterial wall on postoperative day 28, rapamycin did not reach levels associated with systemic toxicity. Rapamycin was not detectable in blood after postoperative day 3.

TABLE IV

Quantification of Rapamycin Drug Levels in Graft, Artery and Blood

| Rapamycin | Day 0 | Day 1 | Day 2 | Day 3 | Day 7 | Day 14 | Day 28 |
|---|---|---|---|---|---|---|---|
| Graft (μg) (n = 3) | 1000 | N/A | N/A | N/A | 26.7 ± 1.4 | 12.8 ± 5.0 | 0.005 ± 0.001 |
| Artery (μg/gm) (n = 3) | 0 | N/A | N/A | N/A | 2.9 ± 0.8 | 1.3 ± 0.2 | 0.025 ± 0.007 |
| Blood (ng/ml) (n = 3) | 16.9 ± 1.8 | 9.3 ± 0.2 | 2.0 ± 0.1 | 1.9 ± 0.2 | 0 | 0 | 0 |

Intimal hyperplasia is initiated by endothelial damage. Neointimal hyperplasia represents the response of vascular smooth muscle cells (VSMCs) to physical, chemical and humoral factors in regions of dysfunctional endothelial regulation. Vascular smooth muscle cells are induced to migrate from the media to the intima where they proliferate and deposit extracellular matrix (ECM) (Lemson et al., "Intimal Hyperplasia in Vascular Grafts," *Eur. J. Vasc. Endovasc. Surg.* 19:336-50 (2000), which is hereby incorporated by reference in its entirety). Research on the development of neointimal hyperplasia has focused on the prevention of arterial restenosis following percutaneous transluminal angioplasty (PTA) and implantation of vascular grafts. The endothelium is disrupted at vascular anastomoses and at sites of PTA. Use of stents can prevent recoil and remodeling in treated arteries but does not eliminate neointimal hyperplasia. Struts from implanted stents incite an inflammatory response in the adjacent artery. This response perpetuates restenosis by initiating cytokine release from infiltrating cells. Vascular grafting with ePTFE also elicits neointimal hyperplasia through alterations in wall shear, flow and compliance mismatch between the native artery and the prosthetic (Lemson et al., "Intimal Hyperplasia in Vascular Grafts," *Eur. J. Vasc. Endovasc. Surg.* 19:336-50 (2000); Weston et al., "Compliance and Diameter Mismatch Affect the Wall Shear Rate Distribution Near an End-to-End Anastomosis," *J. Biomech.* 29:187-98 (1996); Loth et al., "Relative Contribution of Wall Shear Stress and Injury in Experimental Intimal Thickening at PTFE End-to-Side Anastomoses," *J. Biomech. Eng.* 124:44-51 (2002), each of which is hereby incorporated by reference in its entirety).

Pharmacologic manipulation of VSMC migration, proliferation and ECM production represents one approach in the treatment of restenosis after vascular intervention. Rapamycin is a macrocyclic, lipophilic lactone with immunosuppressive antibiotic activity derived from the actinomycete *Strep-*

*tomyces hygroscopicus.* Rapamycin is approved by the United States Food and Drug Administration (FDA) for the prophylaxis of renal transplant rejection. Rapamycin has many properties that make it a good agent to counteract neointimal hyperplasia. Rapamycin binds to its cytosolic receptor FK506 binding protein (FKBP-12) and inhibits the mammalian target of rapamycin (mTOR). mTOR is a ubiquitous signal transduction kinase that is responsible for cell cycle progression. mTOR inactivation results in reduction of cyclin dependent kinases (CDK) and increased levels of p27kip1, a cyclin dependent-kinase inhibitor (CDKI). The net effect is to cause G1-S arrest in proliferating cells such as T cells and VSMCs (Gallo et al., "Inhibition of Intimal Thickening After Balloon Angioplasty in Porcine Coronary Arteries by Targeting Regulators of the Cell Cycle," *Circulation* 99:2164-70 (1999); Regar et al., "Stent Development and Local Drug Delivery," *Br. Med. Bull.* 59:227-48 (2001), each of which is hereby incorporated by reference in its entirety). In addition to inhibition of cellular proliferation, rapamycin inhibits migration of VSMCs into areas of vascular injury (Suzuki et al., "Stent-based Delivery of Sirolimus Reduces Neointimal Formation in a Porcine Coronary Model," *Circulation* 104:1188-93 (2001), each of which is hereby incorporated by reference in its entirety). In pigs, rapamycin needs to be present in the vessel wall for 14 days after injury to be efficacious (Sousa et al., "Sustained Suppression of Neointimal Proliferation by Sirolimus-eluting Stents: One-year Angiographic and Intravascular Ultrasound Follow-up," *Circulation* 104:2007-11 (2001); Virmani et al., "Drug Eluting Stents: Are Human and Animal Studies Comparable?" *Heart* 89:133-8 (2003), each of which is hereby incorporated by reference in its entirety). The rate of neointimal proliferation in stented porcine coronary arteries is greatest at fourteen days post injury. The neointima at this point begins to become populated by VSMCs in a proteoglycan-rich matrix. To be effective, rapamycin needs to be present during the time when the stimulus for VSMC migration and proliferation exists. Hydrophobic drugs like rapamycin may achieve higher mean tissue concentrations in the intima because they are less likely to diffuse back into the circulation, thus facilitating longer exposure in the area of injury (Hwang et al., "Physiologic Forces Governing Drug Distribution for Stent-based Delivery," *Circulation* 104:600-5 (2001); Ellozy et al., "Drug-eluting Stents in Peripheral Vascular Disease: Eliminating Restenosis," *Mount Sinai J. Med.* 70:417-9 (2003), each of which is hereby incorporated by reference in its entirety).

Drug elution has been utilized with excellent results in coronary interventions. Paclitaxel and rapamycin-eluting stents significantly reduce the incidence of restenosis and late loss of arterial luminal diameter. Major adverse cardiac events (MACE) such as myocardial infarction, death and target lesion/vessel revascularization are also decreased with drug-eluting stents (Shafiq et al., "A Meta-analysis of Clinical Trials of Paclitaxel- and Sirolimus-eluting Stents in Patients with Obstructive Coronary Artery Disease," Br. J. Clin. Pharmacol. 59:94-101 (2004); Hill et al., "Drug-eluting Stents: An Early Systematic Review to Inform Policy," *Eur. Heart J.* 25:902-19 (2004), each of which is hereby incorporated by reference in its entirety). Patients treated with bare metal stents require more frequent coronary interventions. There is no difference in mortality or incidence of acute myocardial infarction, but studies to date have not included data to detect changes in these endpoints (Hill et al., "Drug-eluting Stents: An Early Systematic Review to Inform Policy," *Eur. Heart J.* 25:902-19 (2004), which is hereby incorporated by reference in its entirety). Review of the literature indicates that drug-eluting stents reduce event rates by 40-60% at 12 months (Hill et al., "Drug-eluting Stents: An Early Systematic Review to Inform Policy," *Eur. Heart J.* 25:902-19 (2004), which is hereby incorporated by reference in its entirety).

Drug-eluting stents have not performed as well in the infrainguinal circulation. Stenoses and occlusions are more common in the femoropopliteal region than in the coronaries. In addition, lesions here tend to be multiple, long, heavily calcified and endophytic. Approximately 90% of the time, peripheral arteries can undergo successful angioplasty, but, recurrence is common, with restenosis occurring up to 80% after one year. Stenting femoropopliteal vessels after balloon angioplasty has not substantially improved patency. Nitinol stents may improve these results as they are less prone to external compression and elicit less neointimal hyperplasia than more rigid balloon expandable stents (Dorrucci, "Treatment of Superficial Femoral Artery Occlusive Disease," *J. Cardiovasc. Surg.* 45:193-201 (2004); Muradin et al., "Balloon Dilatation and Stent Implantation for Treatment of Femoropopliteal Arterial Disease:Meta-analysis," *Radiology* 221:137-45 (2001); Fontaine et al., "Stent-induced Intimal Hyperplasia Are There Fundamental Differences Between Flexible and Rigid Stent Designs?" *J. Vasc. Interv. Radiol.* 1994:739-44; Ruef et al., "Endovascular Intervention in Iliac and Infrainguinal Occlusive Artery Disease," *J. Interven. Cardiol.* 17:427-35 (2004), each of which is hereby incorporated by reference in its entirety). Sirolimus(rapamycin)-eluting, nitinol-expandable SMART™ stents in the peripheral circulation have been evaluated in two trials. These trials are identified by the acronym SIROCCO, which stands for SIROlimus Coated Cordis SMART™ nitinol self-expandable stent for the treatment of Obstructive superficial femoral artery disease. SIROCCO I had promising early results with 0% restenosis in the drug-eluting arm at 6 months, however stent fractures were reported in 6 of 33 patients, 3 in each treatment group (Duda et al., "Sirolimuseluting Stents for the Treatment of Obstructive Superficial Femoral Artery Disease: Sixmonth Results," *Circulation* 106:1505-9 (2002), which is hereby incorporated by reference in its entirety). The 18 month results were mixed, with the slow-eluting rapamycin stent having 0% restenosis, but the fast eluting stent having 33% restenosis. By 24 months, both slow and fast-eluting coated stents failed to show a difference from uncoated stents and had a binary restenosis of 40% (Das, "Optimal Therapeutic Approaches to Femoropopliteal Artery Intervention," *Catheter. Cardiovasc. Interv.* 63:21-30 (2004), which is hereby incorporated by reference in its entirety). The SIROCCO II trial 18 month data also failed to show superiority, with a total in-stent binary restenosis rate of 20.7% for the rapamycin-eluting stent and 17.9% for the uncoated stent arm. Stents in peripheral arteries of the lower extremities treat longer, more calcified lesions in arteries with relatively low flow rates. Stents in the periphery experience increased biomechanical forces including elongation, rotation and radial compression due to anatomy of the femoropopliteal vasculature. The attendant stent deformation may result in stent fractures and neointimal proliferation (Allie et al., "Nitinol Stent Fractures in the SFA," *Endovasc. Today* 3:22-34 (2004), which is hereby incorporated by reference in its entirety). The greater propensity for neointimal hyperplasia may require higher levels of drug than can be eluted locally from coated stents. Also, the use of self-expanding stents presents new challenges for drug loading and delivery that do not pertain to coronary stent technology and which may limit dose of available drug. Some might question the impetus to pursue improvement in peripheral circulation stenting in view of the relative success that has been achieved by open surgery. The 70-80% 5-year patency achieved with bypass surgery (vein and prosthetic) may be hard to surpass (Comerata, "Endovascular and Surgical Revascularization for Patients with Intermittent Claudication," *Am. J. Cardiol.* 87:34 D-43D (2001), which is hereby incorporated by reference in its entirety).

While metal alloy technology is optimized so as to decrease propensity for stent deformation and fracture, the need to improve performance of prosthetic grafts is still warranted. Prosthetic grafts are not prone to structural damage and maintain excellent handling characteristics, but small diameter (<6 mm) grafts are prone to thrombosis. Low shear and flow separation at prosthetic anastomoses cause release of growth factors that result in VSMC proliferation (Lemson et al., "Intimal Hyperplasia in Vascular Grafts," *Eur. J. Vasc Endovasc. Surg.* 19:336-50 (2000); Loth et al., "Relative Contribution of Wall Shear Stress and Injury in Experimental Intimal Thickening at PTFE End-to-Side Anastomoses," *J. Biomech. Eng.* 124:44-51 (2002), each of which is hereby incorporated by reference in its entirety). Coating methods that exploit the hydrophobic nature of the graft and the electronegativity of the graft surface while avoiding denaturation of the pharmacologic agent used to modify neointimal hyperplasia are necessary so that thrombo-resistance and biocompatibility of the ePTFE can be maintained.

In the current experiments, the reduction in neointimal hyperplasia seen with the rapamycin-eluting ePTFE grafts is encouraging because the maintenance of anastomotic length and decreased percentage of cross sectional narrowing may translate to improved patency, especially in small diameter ePTFE grafts that are most prone to failure. Equally as important is the fact that the coating process does not appear to influence thrombogenicity or alter arterial healing as evidenced by complete endothelialization in all experimental groups. The results need to be evaluated at longer time intervals, because despite apparent safety, the efficacy seen at twenty-eight days may not persist. Carter et al found that rapamycin-eluting stents inhibited intimal hyperplasia for 30 days; however, long-term inhibition was not sustained presumably because cellular proliferation occurred despite increased levels of p27kip1 (Carter et al., "Long-term Effects of Polymer-based, Slow-release, Sirolimus-Eluting Stents in a Porcine Coronary Model," *Cardiovascular Research* 63:617-24 (2004), each of which is hereby incorporated by reference in its entirety). In their work, rapamycin remained present in the arterial wall (0.32 ng/mg) at 90 days, however, although increased levels of p27kip1 were detected, there was also increased expression of proliferating cell nuclear antigen (PCNA) raising the possibility that there were factors stimulating neointimal formation that were not inhibited by rapamycin effects on the cell cycle (Braun-Dullaeus et al., "Cell Cycle Protein Expression in Vascular Smooth Muscle Cells in vitro and in vivo Is Regulated Through Phosphatidylinositol 3-Kinase and Mammalian Target of Rapamycin," *Arterioscler. Thromb. Vasc. Biol.* 21:1152-8 (2001); Sun et al., "Role of p27kip1 in Vascular Smooth Muscle Cell Migration," *Circulation* 103:2967-72 (2001); Diez-Juan et al., "Coordinate Control of Proliferation and Migration by the p27kip1/Cyclin-dependent Kinase/Retinoblastoma Pathway in the Vascular Smooth Muscle Cells and Fibroblasts," *Circ. Res.* 92:402-10 (2003), each of which is hereby incorporated by reference in its entirety). In the present experiment, rapamycin was deposited in the adjacent arterial wall on postoperative day 7 (2.9 ng/mg or 2.9 µg/gm). At euthanasia, arterial levels of rapamycin had decreased to 0.025 ng/mg. The continued suppression of neointimal hyperplasia despite a 10-fold decrease in drug concentration when compared with Carter et al, raises questions about minimum dose and duration of exposure that are required for initiation and maintenance of rapamycin's therapeutic effect. It is not known what minimal tissue level of rapamycin needs to be present to achieve a measurable decrease in neointimal hyperplasia. The current therapeutic rapamycin level (8-17 ng/ml) is derived from blood of patients being prophylaxed against kidney transplant rejection. Low tissue levels, as evidenced by lack of rapamycin detection in blood after postoperative day three, make systemic toxicity unlikely.

Another cautionary note pertains to the extrapolation of data from a porcine model to humans. The response of peripheral porcine arteries to injury is not as well characterized and appears to be less vigorous than in coronary arteries (Schwartz et al., "Preclinical Evaluation of Drug-eluting Stents for Peripheral Applications: Recommendations from an Expert Consensus Group," *Circulation* 110:2498-505 (2004), which is hereby incorporated by reference in its entirety). Humans and pigs exhibit differences in their responses to rapamycin. When preclinical studies showing a 50% reduction in neointimal formation at 30 days, early human trials showed 80-90% inhibition at 6 months (Morice et al., "A Randomized Comparison of a Sirolimus-eluting Stent with a Standard Stent for Coronary Revascularization," *N. Engl. J. Med.* 346:1773-80 (2002), which is hereby incorporated by reference in its entirety). The discrepancy may be explained by differences in species arterial wall substrate. Human trials consisted of atherosclerotic vessels that have more abundant FKBP-12 receptor, whereas, porcine arteries were normal and had lower levels of FKBP-12 (Carter et al., "Long-term Effects of Polymer-based, Slow-release, Sirolimus-Eluting Stents in a Porcine Coronary Model," *Cardiovascular Research* 63:617-24 (2004); Zohlnhofer et al., "Gene Expression Profiling of Human Stent Induced Neointima by cDNA Array Analysis of Microscopic Specimens Retrieved by Helix Cutter Atherectomy: Detection of FK506-binding Protein 12 Upregulation," *Circulation* 103:1396-402 (2001), each of which is hereby incorporated by reference in its entirety). Pigs may represent a tougher model to demonstrate decreases in neointimal hyperplasia with rapamycin because of their relative paucity of rapamycin receptors. Paclitaxel-eluting stents used in porcine models have also shown modest changes in neointimal hyperplasia. Preclinical porcine data for the TAXUS SR™ stent failed to show reduction in neointimal hyperplasia at 28 to 180 days, whereas, human clinical data showed reduction in restenosis at 9 months and a maintenance of effect up to three years post drug-eluting stent implantation (Stone et al., "A Polymer-based, Paclitaxel-eluting Stent in Patients with Coronary Artery Disease," *N Engl. J. Med.* 350:221-31 (2004), which is hereby incorporated by reference in its entirety). Regardless of the limitations, porcine coronary arteries respond to injury by producing a neointima within 28 days that is similar to humans. The amount of neointima produced is proportional to the degree of injury (Schwartz et al., "Preclinical Restenosis Models and Drug-eluting Stents—Still Important, Still Much to Learn," *J. Am. Coll. Cardiol.* 44:1373-85 (2004), which is hereby incorporated by reference in its entirety). Despite limitations in establishing efficacy, the porcine model is good at establishing safety of an intervention (Schwartz et al., "Preclinical Restenosis Models and Drug-eluting Stents—Still Important, Still Much to Learn," *J. Am. Coll. Cardiol.* 44:1373-85 (2004), which is hereby incorporated by reference in its entirety).

The results of the present study confirm the feasibility and safety of coating ePTFE with rapamycin. At twenty-eight days, rapamycin-eluting ePTFE grafts demonstrate diminished gross, pathologic and morphometric features of neointimal hyperplasia. These results are with early evaluation of neointimal hyperplasia post implantation and need to be assessed with longer follow-up to confirm maintenance of efficacy. The data from the present study supports the deposition of locally eluted rapamycin into the arterial wall and its persistence in the artery even after drug has been eluted from the prosthetic (see Table IV above). Pharmacologic inhibition of VSMC function by rapamycin needs to be maintained at least until endothelial coverage is achieved at anastomoses. Arterial injury causes endothelial dysfunction and VSMC proliferation, migration, phenotype alteration and ECM deposition during the first two to four weeks in a porcine model. In humans, the period of arterial healing is longer and rapamycin needs to be present and active in peri-anastomotic tissue at least until endothelialization is complete. Alterations in kinetics of rapamycin elution may be required to allow longer exposure of rapamycin to vessels adjacent to treated anastomoses. Unlike metal stents which experience fractures and subsequent neointimal formation when exposed to the biomechanical forces in the femoropopliteal circulation, rapamycin-eluting ePTFE grafts may prove superior because handling characteristics and biocompatibility are preserved. It remains to be seen whether decreased neointimal proliferation with rapamycin-eluting ePTFE grafts will translate into improved patency that will allow more frequent use of prosthetic grafts in situations where autologous material is not available and where neointimal hyperplasia is prevalent.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of delivering a therapeutic agent to a site, said method comprising:
    providing a delivery vehicle; and
    contacting the site with the delivery vehicle wherein the delivery vehicle comprises:
    an implantable polymer body having a surface; and
    a layer of a pharmaceutical formulation contacting the surface of the polymer body;
    wherein the pharmaceutical formulation comprises the product resulting from a mixture comprising bisphenyldimethacrylate, N-tolylglycine-glycidylmethacrylate, and a therapeutic agent.

2. The method according to claim 1, wherein the delivery vehicle is a vascular graft and the contacting of the site occurs at a vessel.

3. The method according to claim 2, wherein the vessel is an artery.

4. The method according to claim 1, wherein the therapeutic agent is present in an amount of between about 10 pg to about 1 g per polymer body.

5. The method according to claim 1, wherein said delivery affords extended release of the therapeutic agent.

6. The method according to claim 5, wherein the extended release occurs in a period of about 2 days to about 6 months.

7. The method according to claim 1, wherein the therapeutic agent is selected from the group of rapamycin, an anti-inflammatory agent, an antimicrobial agent, an antibacterial agent, an antifungal agent, an anti-thrombogenic agent, an anti-proliferative agent, and mixtures thereof.

8. A method of inhibiting restenosis or neointimal hyperplasia of a vascular graft, said method comprising performing the method according to claim 2 wherein release of the therapeutic agent inhibits restenosis or neointima formation within the vascular graft.

9. The method of claim 2, wherein the therapeutic agent is released at the vessel.

10. The method of claim 1 wherein the polymer of the polymer body is expanded polytetrafluoroethylene (ePFTE).

11. The method of claim 2, wherein the therapeutic agent inhibits development of an infection at the vessel.

* * * * *